United States Patent [19]

Eichhorn

[11] Patent Number: 5,078,729

[45] Date of Patent: Jan. 7, 1992

[54] TICK REMOVAL TOOL

[76] Inventor: Heino F. Eichhorn, P.O. Box 399, Rogue River, Oreg. 97537

[21] Appl. No.: 584,580

[22] Filed: Aug. 30, 1990

[51] Int. Cl.$^5$ ............................................. A61B 17/28
[52] U.S. Cl. .................................. 606/210; 294/99.2
[58] Field of Search ............... 606/157, 158, 205, 206, 606/207, 208, 209, 210, 211, 151, 131; 294/99.2, 100

[56] References Cited

U.S. PATENT DOCUMENTS

| | | | |
|---|---|---|---|
| 1,033,942 | 7/1912 | Ruggles | 606/210 |
| 1,461,670 | 7/1923 | Mills | 294/99.2 |
| 3,259,415 | 7/1966 | Howard | 294/99.2 |
| 3,321,736 | 5/1967 | Flynn | 294/99.2 |
| 4,213,460 | 7/1980 | Weiner | |
| 4,442,837 | 4/1984 | Keatley | |
| 4,976,718 | 12/1990 | Daniell | 606/210 |

OTHER PUBLICATIONS

Automobile Trade Journal; July 1913; p. 112.

Primary Examiner—C. Fred Rosenbaum
Assistant Examiner—William Lewis

[57] ABSTRACT

A pair of elongated interlocked pivotal clamping members having opposing, normally closed, openable jaws structured for enclosing the body of an embedded tick within a cavity formed between the closed jaws. One jaw has a semicircular notch centered with the cavity. The notch forms an aperture when the jaws are closed. The aperture is sized for snug fitting placement over the neck of the tick to hold and prevent severing of the tick's neck. One clamping member is affixed with a compression spring which abuts the opposing clamping member to maintain the jaws in a normally closed position. Both clamping members gradually widen from the jaw end to the oppositely disposed ends thereof, which are affixed with widened finger or gripping plates for easy handling.

1 Claim, 6 Drawing Sheets

TICK REMOVAL TOOL

BACKGROUND OF THE INVENTION

1. Field of the Invention

This invention relates to an improved device for safely removing parasites, namely ticks, from a person or animal.

2. Description of the Prior Art

Ticks have long been a problem not only with animals but humans as well. Ticks characteristically embed their heads into the host's skin with the use of sharp barbs and remain attached while feeding on the host's blood. The most common method of removal in the past has been to manually pull the tick from the host. This method most often results in the tick's head being broken off and embedded in the skin when the body is pulled free. Unfortunately, leaving the head in the wound can result in infection. Also, manually removing the tick with the fingers often results in the tick being smashed, forcing some of the internal fluids of the tick back into the wound, which can aid in the transfer of disease, as well as localized infection in the wound. It has been found ticks are more readily extracted when first rotated back and forth several times. This allows the tick to release its grip and be pulled free from the wound, head intact. Several devices have been provided over the years for the purpose of removing embedded ticks. The majority of these devices however, are fairly complicated to operate requiring two handed manipulation of the device, with some requiring constant pressure on a clamp or lever during the procedure. Since many animals, and some children, find it difficult to sit still for even a short period of time while the tick is removed, the user must hold the host with one hand and manipulate the tick removal device with the other. This makes the operation of the removal device extremely difficult if it requires more than one or two minor manipulations to extract the tick. Therefore, there is a need for a simple, inexpensive tick removal tool having the following qualities: a device which can be operated with one hand without the user's initial grip ever being changed, the device will remain engaged onto the embedded tick should the user loose his grip, and a tool which will not sever the neck of the embedded tick nor crush the body of the tick during extraction.

SUMMARY OF THE INVENTION

I have provided a plastic tick removal tool which can easily be used with one hand. The device is an openable clamp structure having a compression spring to hold two pivotally attached clamping jaws normally closed at one end. The jaws are structured to engulf and secure the body of the tick inside a cavity of the jaw structure, without crushing the tick or severing the tick's neck and head. The enclosing jaws also prevent the tick from sliding out sideways. A semicircular notch is formed in a terminal end wall of one jaw, which, with the jaws in the closed position, in conjunction with the opposing jaw forms an aperture centrally aligned with the cavity of the tool. The aperture is for placement around a tick's neck.

To operate the tool, the jaws are opened by pressing on finger grips of the tool with two finger of one hand to defeat the compression spring, and centering the tip of the jaws over the protruding body of the tick with the tick's neck positioned within the notch. A guidance arrow on the top on one jaw helps visually align the notch with the neck of the tick. Finger pressure on the grips is then relieved, and the compression spring closes and maintains the jaws over the tick to incase the tick's body inside the interior cavity of the jaws. With the jaws closed over a tick, the neck is positioned within the central aperture in the tip of the jaws, and the head of the tick is outside of the tool and embedded in the skin of the animal. The central aperture in the tip of the tool is sized small enough to form a snug fit around the tick's neck, but not so constricting as to cause severing of the head. The body of an engorged tick will fit within the interior cavity formed by the jaws, holding the body of the tick secure. The central positioning of the aperture relative to the cavity of the jaws allows the body of the tick to be in straight alignment with the neck, thereby helping to prevent severing of the neck and head. Smaller, un-engorged ticks can also be easily removed with this device, as the neck of any given variety of adult tick does not vary appreciably in size whether the tick is engorged or not. Since the neck size of the tick remains substantially the same diameter, and the aperture of the tool is sized to lightly grasp the neck, the neck will be held sufficiently secure by the aperture to allow rotation. When the tool is placed over an embedded tick, the relatively thin terminal end walls of the tips of the jaws are positioned between the skin of the animal and the relatively large tick body, with the relatively large tick body being compared to the small diameter neck of the tick within the central aperture of the tool.

Once the tool has been properly placed over the tick, the tool is manually rotated simultaneously with gently pulling to remove the tick without severing the tick's head. Usually, a half circle rotation is all that is necessary coupled with gentle pulling to pull the head of the tick from the skin. The rotational movement should begin slightly prior the pulling action. It is the combination of the light pressure on the tick's neck by the central aperture with the friction and abutment of the jaw end walls against the tick's shoulders or body which allows rotation of the tick, in combination with pulling motion using the abutment of the jaw end walls against the tick's body which allows predictable removal of the tick.

Some of the most important features of this device include ease in operation and an almost infallible success rate with removing a tick without severing the head of the tick. Also, only one hand is needed to carry out the whole procedure. This enables the whole procedure to be carried out with only one hand, leaving the other hand free to hold the animal or host if needed. If the user inadvertently looses his grip on the tool, the tool will remain attached to the tick due to the normally closed jaws, and the light weight of the tool will not pull the tick free or sever its head, unless it is already sufficiently disengaged.

Since varieties of adult ticks in certain geographical areas are larger than adult ticks of other varieties, it may be necessary during manufacturing to size certain parts of the tick removal tool such as the center aperture and cavity commensurate with a given variety of adult tick, however, the structure of the tool would remain essentially the same.

Therefore, the major object of my invention is to provide a tick removal tool which is quick and simple to use with a single hand, and removes the tick with the head intact.

A further object of the invention is to provide a tick removal tool which does not crush the body of the tick by providing a cavity in which to hold the body of the tick in alignment with the retained neck of the tick.

Another object of the invention is to provide a tick removal tool which does not require the user to alter his initial grip, thereby being easier to operate.

A still further object of the invention is to provide a tick removal tool which is inexpensive to manufacture, being suitable for manufacture with modern thermoplastic injection molding techniques.

Other objects and advantages of my invention will become apparent from a reading of the remaining specification and comparison with the accompanying numbered drawings.

DESCRIPTION OF THE PREFERRED EMBODIMENT

Figure 1:
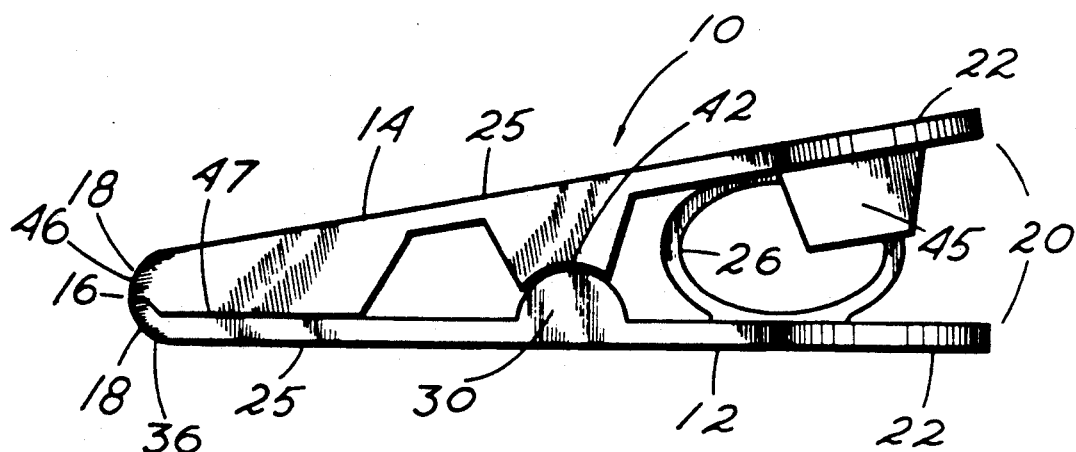
FIG. 1 is a left side view of the assembled tick removal tool.

Referring now to the drawings where the preferred embodiment of my tick removal tool 10 is illustrated. My tick tool 10 is preferably manufactured entirely of thermoplastic material such as polycarbonate, polypropylene or polyethylene for example, and molded using automated plastic injection technology to allow the tool 10 to be made both inexpensively and lightweight. Tick removal tool 10 is comprised of two interlocking pivotal clamping members, first member 12 and second member 14. Each member 12 and 14 is roughly comprised of an elongated plate, narrow and rounded at one terminal end and gradually widening to the oppositely disposed terminal end. The narrow end of both members 12 and 14, designated first end 16, are structured to form two opposing jaws 18 when assembled. The larger end of both members 12 and 14, designated second end 20, widens into large flat circular gripping plates 22. Each member 12 and 14 has an interior surface 24 and an exterior surface 25, with interior surfaces 24 being adjacent but spaced apart relative to one another when assembled. For descriptive purposes in this specification, first member 12 is positioned on the bottom when assembled, with second member 14 positioned on the top. When in actual use however, the orientation of members 12 and 14 is not critical, as long as the device is generally longitudinally aligned with the body of tick 52.

First member 12 and second member 14 are sized equal in length and width. First member 12 is affixed on the upper or interior surface 24 with a flexible annular ring or compression spring 26. Compression spring 26 is a resilient band or ring which is inherently molded onto interior surface 24 adjacent second end 20, with the entire tick removal tool 10 being manufactured of plastic.

Centrally located on interior surface 24 of first member 12 is attachment pin assembly 28. Attachment pin assembly 28 consists of a halved cylindrical base 30 positioned transversely on first member 12, supporting a vertical post 32 with a top spherical retainment knob 34. First end 16 of first member 12 is structured to function in cooperation with first end 16 of second member 14 as clamping jaws 18. First end 16 of first member 12 is rounded and contains a thin upwardly curved terminal end wall 36, best shown in FIG. 6. Exterior surface 25 of gripping plate 22 contains transverse striations or knurled surface 38, for better gripping traction.

Figure 2:
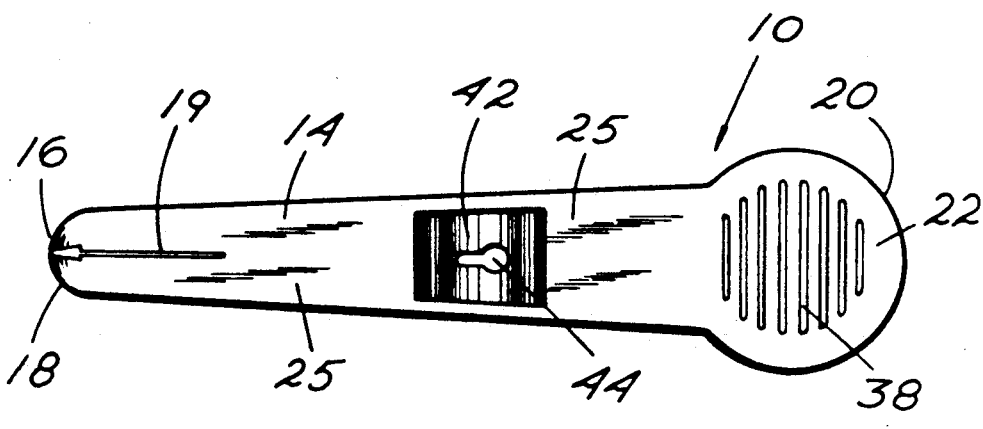
FIG. 2 is a top plan view thereof.
Figure 3:
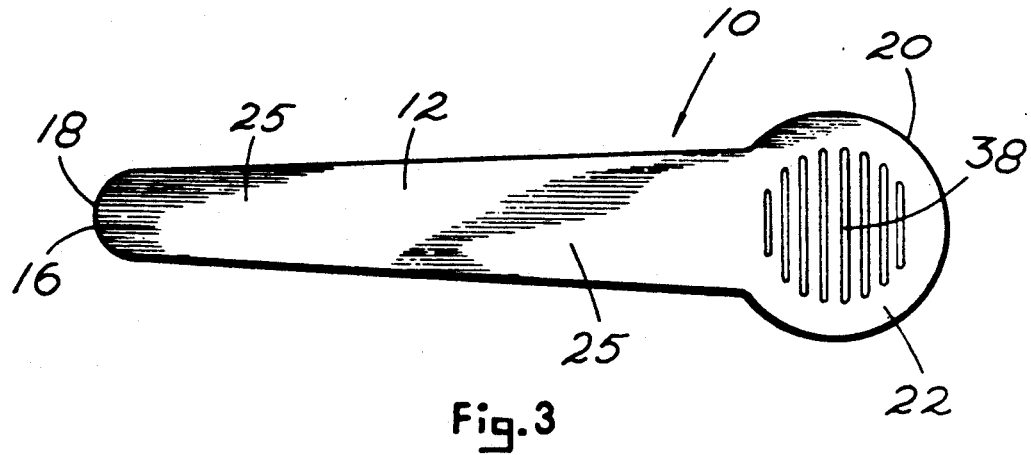
FIG. 3 is a bottom plan view of the assembled invention.
Figure 4:
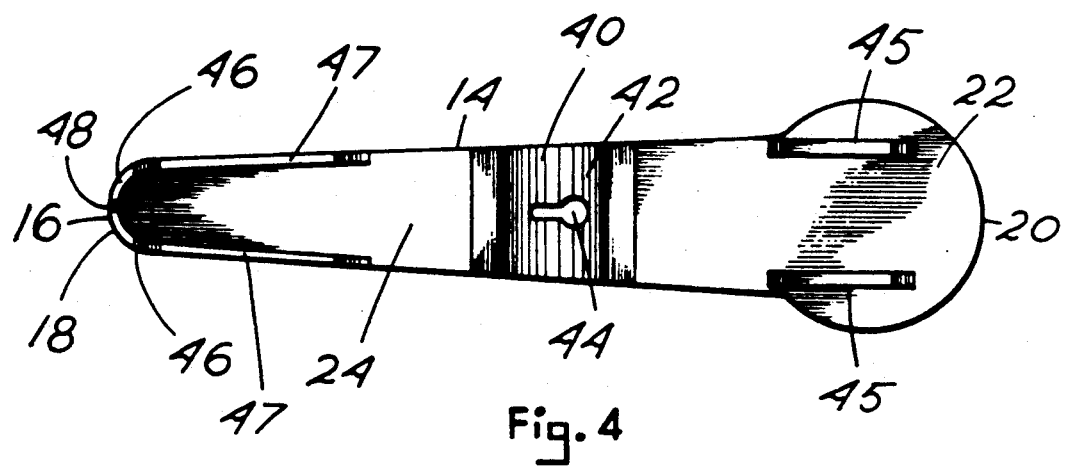
FIG. 4 is a bottom plan view of the top or second member of the tick removal tool.
Figure 5:
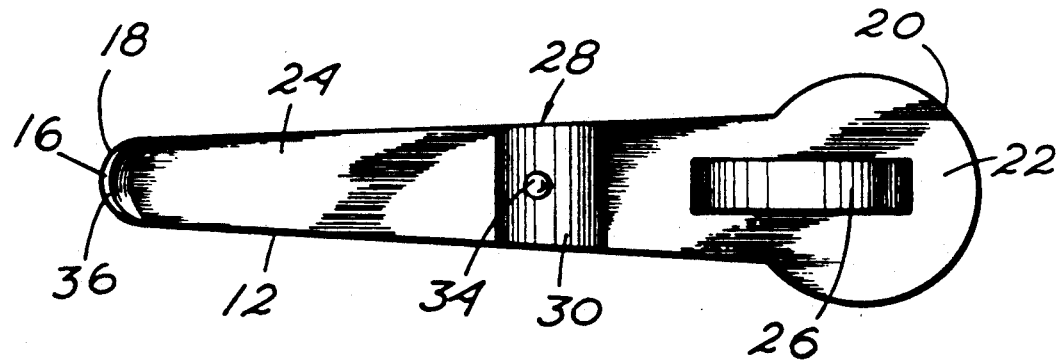
FIG. 5 is a top plan view of the bottom or first member of the tick removal tool.
Figure 6:
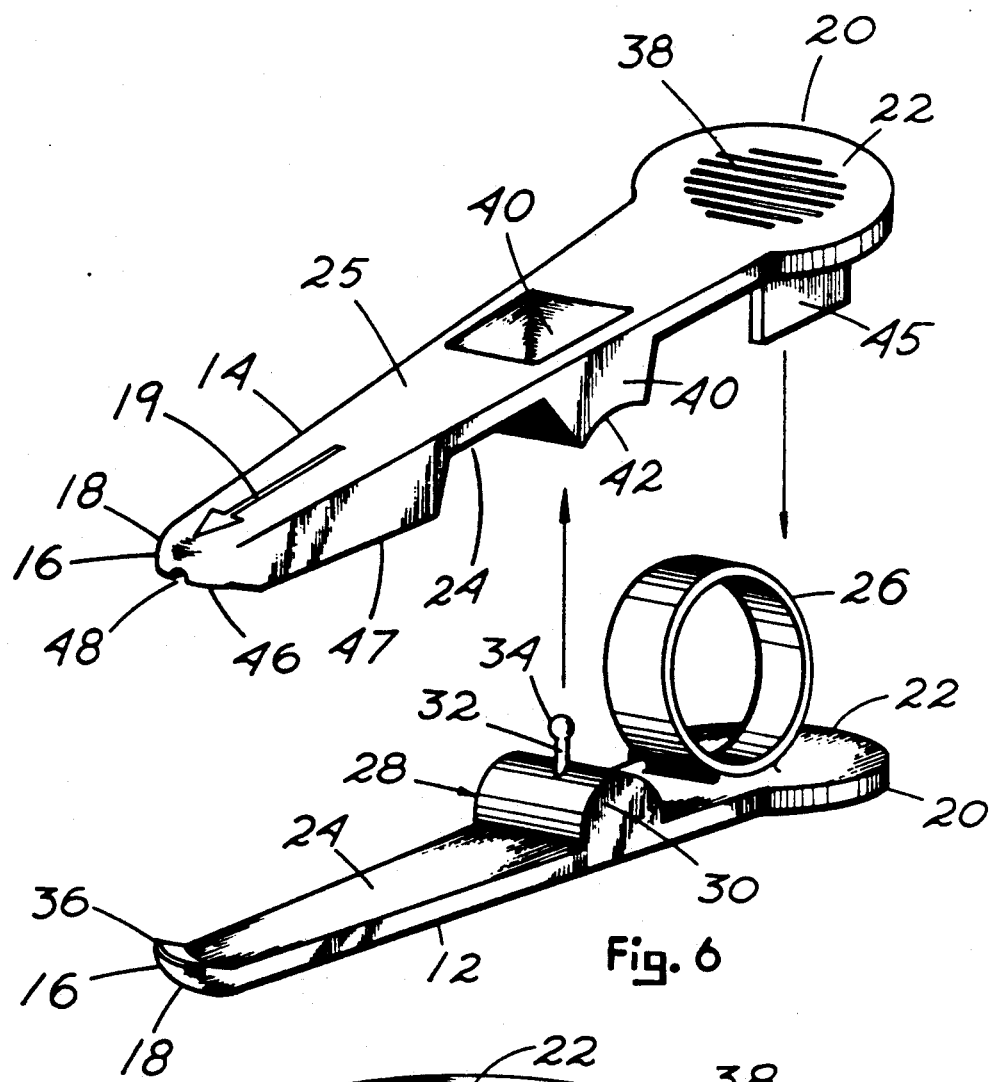
FIG. 6 is a perspective frontal view of the tick removal tool unassembled, illustrating the second member on the top with the first member positioned beneath.
Figure 7:
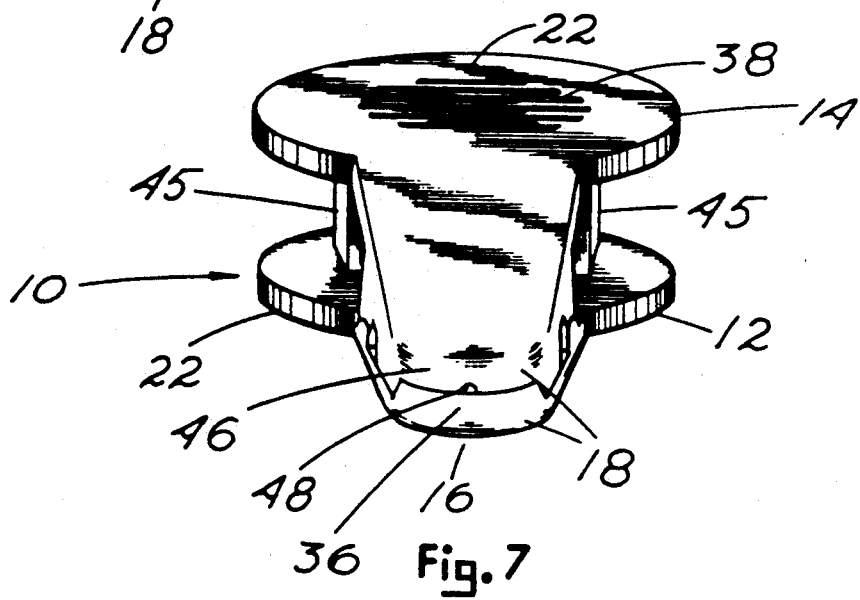
FIG. 7 is an assembled frontal view of the invention illustrating the central neck aperture.
Figure 8:
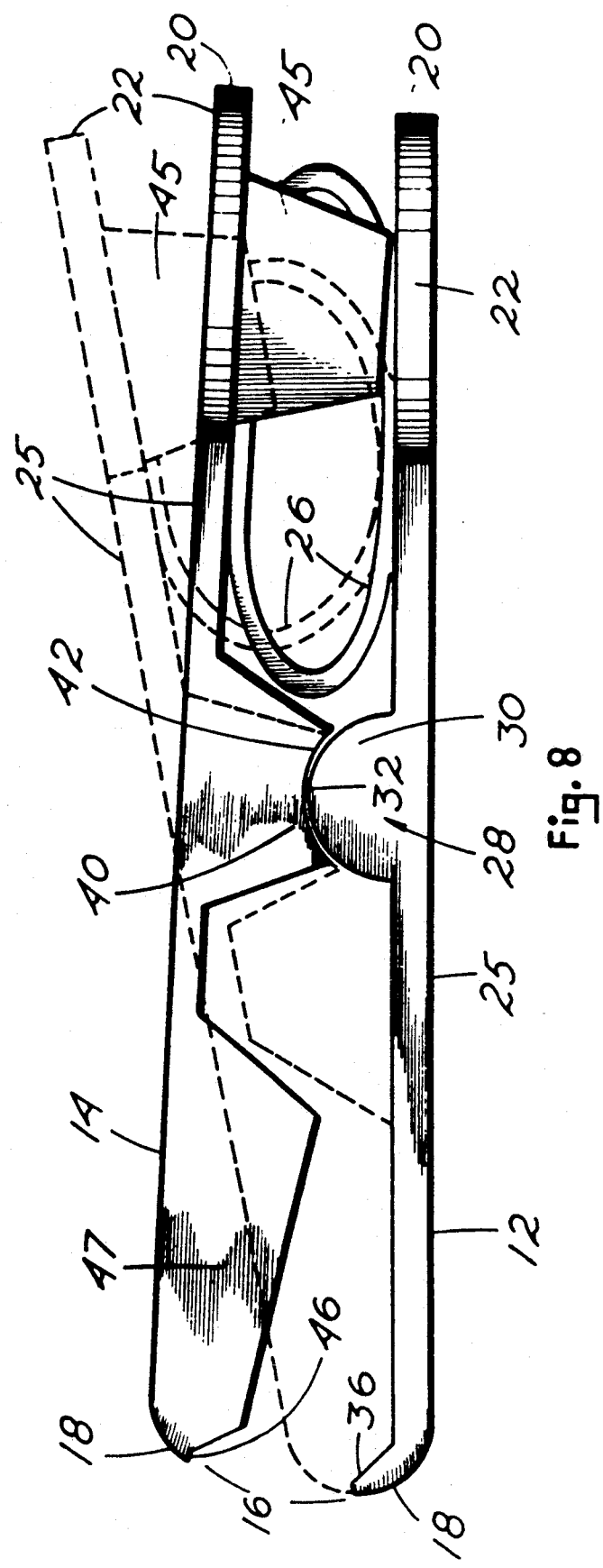
FIG. 8 is an enlarged left side view of the assembled invention illustrating the pivotal placement of the second member in the open position.
Figure 9:
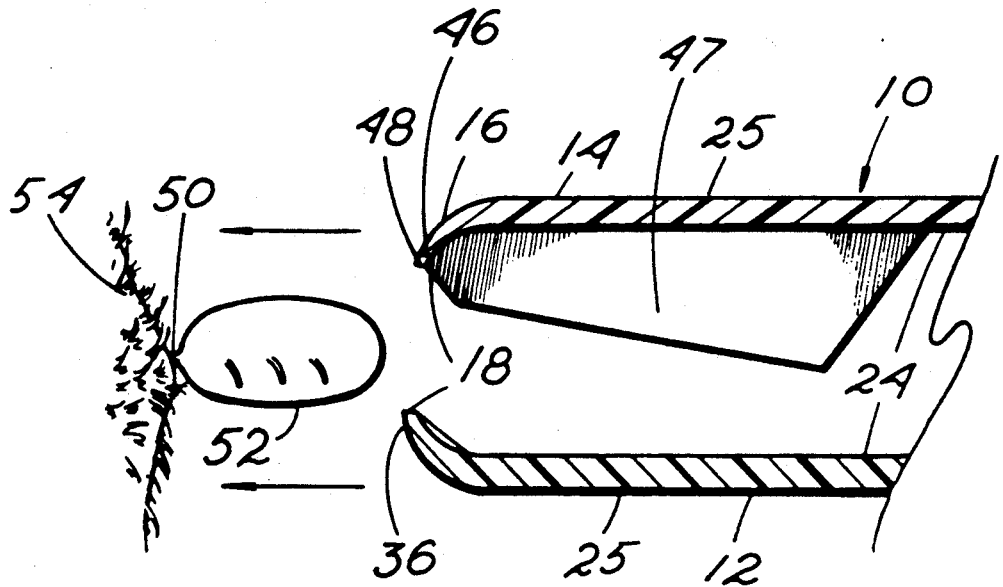
FIG. 9 is an enlarged cross-sectional side view of the jaw portion of the tick removal tool positioned for attachment onto an embedded tick.
Figure 10:
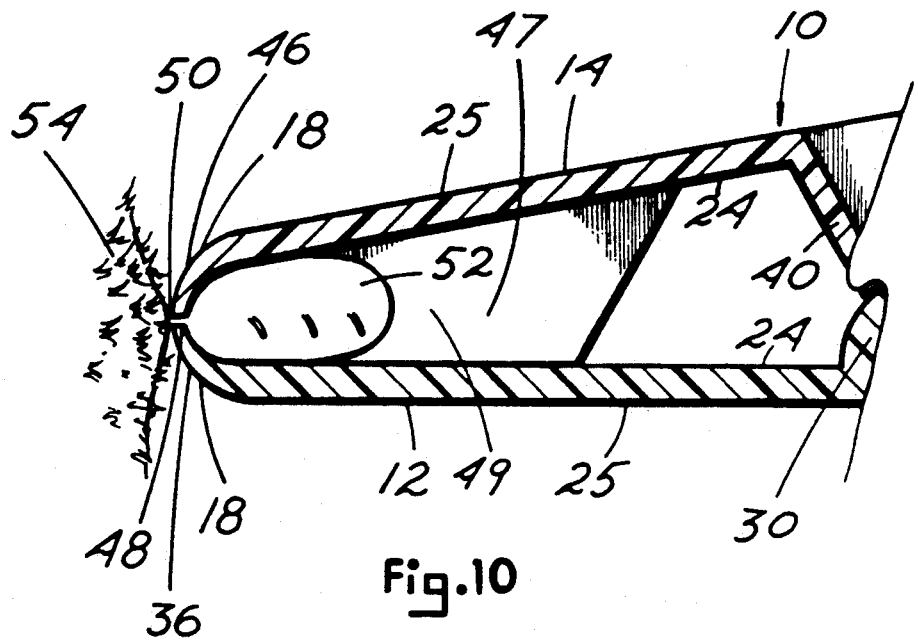
FIG. 10 is an enlarged cross-sectional side view of the jaw portion of the tick removal tool clamped over the embedded tick.
Figure 11:
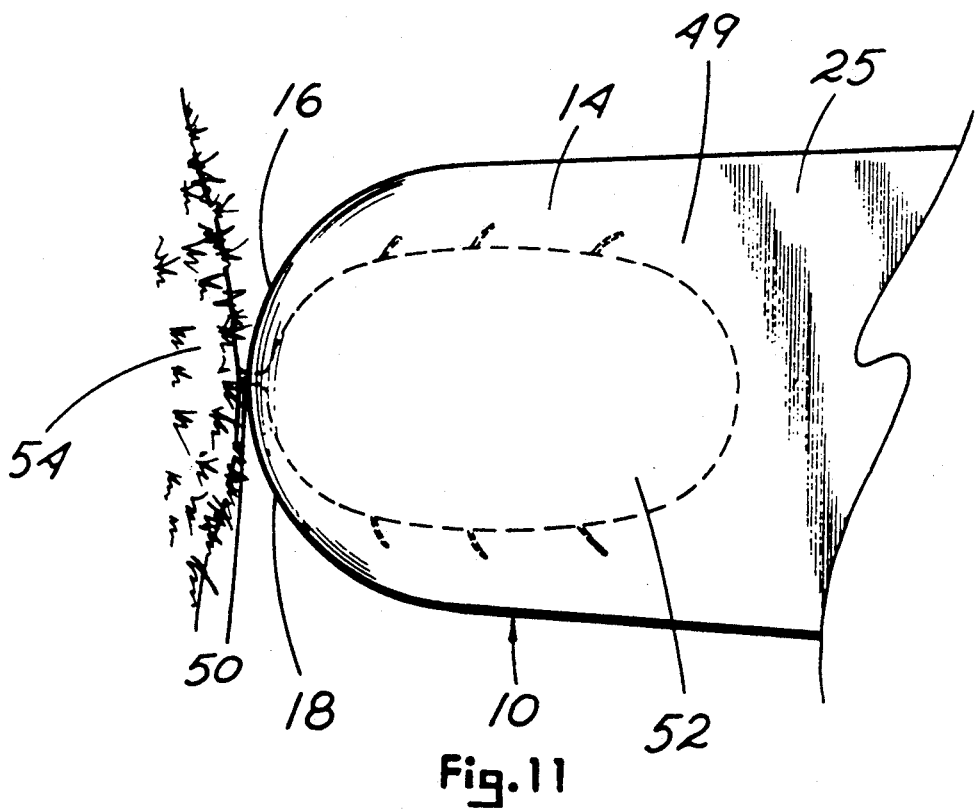
FIG. 11 is an enlarged top view of the jaw portion of the tick removal tool showing, in dotted outline, a tick centered within the cavity between the jaws.

The bottom or interior surface 24 of second member 14 contains a central attachment bracket 40, as shown in FIG. 4 and 6. Attachment bracket 40 is structured to interlock with attachment pin assembly 28 of first member 12. Attachment bracket 40 is roughly structured of a small rectangular hollow bracket having a trough-like curved bottom surface 42 which runs transverse to the longitudinal side edges of second member 14. From exterior surface 25 of second member 14, best seen in FIG. 6, the interior of attachment bracket 40 can be seen as a rectangular depression. Curved surface 42, of attachment bracket 40, contains a central elongated aperture, attachment pin aperture 44, best seen in FIG. 2, which is sized for receiving retainment knob 34 of attachment pin assembly 28. Attachment pin aperture 44 is structured with one side of the elongated aperture having a circular opening sized for receiving retaining knob 34, with a connecting smaller aperture sized for accepting the smaller post 32. This allows initial insertion of the larger retainment knob 34, which once inserted is positioned forward, engaging the narrower post 32 into the smaller portion of attachment pin aperture 44. Retainment knob 34 will prevent the detachment of attachment pin assembly 28 from attachment bracket 40. Curved surface 42 is sized for sliding or pivotal abutment against the curved base 30 of first member 12. When both members 12 and 14 are affixed together in lengthwise parallel alignment, compression spring 26 is slightly compressed between both interior surfaces 24 of members 12 and 14. This provides constant pressure against jaws 18 and maintains them in a normally closed position, while the opposite end of the tool is retained normally open or spaced apart. Also located on interior surface 24 of second member 14, on gripping plate 22, are two stop blocks 45. Each stop block 45 is a flat plate having inwardly sloping side edges, positioned lengthwise on second member 14 parallel to one another. Stop blocks 45 limit the degree to which jaws 18 can be opened by abutting the interior surface 24 of first member 12. Stop blocks 45 also straddle compression spring 26, which helps to prevent lateral movement of second member 14 in relation to first member 12. First end 16 of second member 14 has a walling arrangement depending from interior surface 24, structured of terminal end wall 46 which is connected to two sidewalls 47 which form walling around the rounded front interior tip of first end 16. The central bottom edge of end wall 46, at the distal tip of first end 16 of second member 14, is a notched which forms a semi-circular containment aperture 48 with the jaws closed. Containment aperture 48 is sized for receiving neck 50 of tick 52, and is of a sufficient size to prevent severing of neck 50, yet small enough to grasp the sides thereof and provide frictional engagement. Compression spring 26 is sufficiently strong to maintain jaws 18 closed over a tick, but is not so strong as to sever the neck of a tick which has been misaligned with aperture 48 and is clamped between end walls 36 and 46. With jaws 18 closed and end walls 36 and 46 abutted, a cavity 49 sized to contain an engorged tick body is defined by end wall 46, sidewalls 47, end wall 36, and interior surfaces 24. Interior surfaces 24 at first end 16 are maintained spaced apart by the abutment of the top edges of end walls 36 and 46. Ticks 52 are somewhat tough, and can receive a degree of manipulation without damage, however, one of tick's 52 weak spots would necessarily have to be neck 50. Providing containment aperture 48 centrally in the terminal end of jaws 18 between sidewalls 47 and interior surfaces 24, reserves sufficient space for the tick's neck to be retained in aperture 48 in straight alignment with the tick's body within cavity 49 to prevent severing, which otherwise might result in infection were the head of tick 52 left embedded in the wound.

To remove an embedded tick 52 from a host 54, the user first grasps gripping plates 22, of tick removal tool 10, and compresses gripping plates 22 closer together. Second member 14 pivots on base 30, compressing spring 26 and allowing jaws 18 to separate. The open jaws 18 are then aligned and positioned over the body of tick 52 with the visual assistance of centering guide arrow 19 on the top center of member 14 shown in FIG. 2. Tick removal tool 10 is positioned in linear alignment with tick 52. Containment aperture 48 is aligned over neck 50 of tick 52. Compression on gripping plates 22 is then released, allowing expansion of compression spring 26 and the closing and maintaining of jaws 18 closed over tick 52 with neck 50 of tick 52 enclosed within aperture 48 and the body of tick 52 contained within cavity 49. The user now rotates and pulls tick removal tool 10, maintaining straight alignment, until tick 52 loosens its grip and can be pulled off of host 54.

One significant advantage of my invention is that all stages of the removal procedure can be accomplished with one hand, and without the user adjusting his initial grip. There is also no need to maintain compression since jaws 18 are inherently maintained in a closed position by compression spring 26. This eliminates the user having to reattach tick removal tool 10 onto tick 52 should his fingers inadvertently slip off gripping plates 22. The overhanging terminal end walls 36 and 46 of jaws 18, which enclose tick 52, also help to prevent tick 52 from falling out sideways should tick removal tool 10 be dropped. This can be a significant problem when trying to extract ticks 52 from unruly animals or children. This invention is also inexpensive to manufacture in plastic, since each member 12 and 14 can be produced as a single unit, later to be easily assembled with inherent snap-on attachment means.

Although I have described my invention in detail in the specification, those skilled in the art will realize that certain modifications and alterations can be made in the device without detracting from its function and scope. For instance, compression spring 26 need not be an enclosed loop, but would also function well as a spring if it were a resilient curved tab or a conventional coiled compression spring. Pivotal attachment between members 12 and 14 could also be accomplished with a central axle pin or axle knobs. The device need also not be limited to manufacture in plastic materials only, as various metals can also be substituted. I therefore reserve the right to modify my device insofar as such modifications remain within the scope of the appended claims.

What I claim as my invention:

1. A tool for removing a tick partially embedded in an animal's skin, said tool comprising;
an elongated first member and an elongated second member each having a first end and an oppositely disposed second end, said first member and said second member each made of lightweight thermoplastic material, said first member affixed by pivotal attachment means to said second member with the affixment positioning said members lengthwise parallel with said first ends and second ends generally aligned respectively, said pivotal attachment means positioned between said first ends and said second ends of said members, biasing means attached to one of the said members and in communication with the other said member, said biasing means positioning said first ends normally closed together and said second ends normally in spaced apart relationship from one another, said biasing means being a compressible resilient loop formed of thermoplastic material as an inherent structure of said member to which said biasing means is attached, said second ends of said members each having widened finger placement surfaces to allow pressing said second ends toward one another providing means for compressing said biasing means and causing movement at said pivotal attachment means to separate said normally closed together said first ends, said first ends of said members each having an affixed terminal end wall positioned to abut one another with said first ends in said normally closed position, a notch in at least one said end wall forming an aperture through abutted said end walls, said aperture sized generally commensurate with a tick's neck diameter, said aperture leading generally centrally into a cavity defined by said first ends, said cavity sized to contain an engorged body of a tick with said first ends in said normally closed position, said end walls sufficiently thin in nature to be placeable between an animal's skin and the body of a tick partially embedded in the animal's skin with the tick's neck extending through said aperture in said end walls.

* * * * *